United States Patent [19]
Alt et al.

[11] Patent Number: 6,057,410
[45] Date of Patent: May 2, 2000

[54] POLYMERIC LIGANDS, POLYMERIC METALLOCENES, CATALYST SYSTEMS, PREPARATION, AND USE

[75] Inventors: Helmut G. Alt; Peter Schertl; Bernd Peifer, all of Bayreuth, Germany; Syriac J. Palackal; M. Bruce Welch, both of Bartlesville, Okla.

[73] Assignee: Phillips Petroleum Company, Bartlesville, Okla.

[21] Appl. No.: 09/048,392

[22] Filed: Mar. 26, 1998

Related U.S. Application Data

[62] Division of application No. 08/339,537, Nov. 15, 1994, Pat. No. 5,770,755.

[51] Int. Cl.$^7$ .............................. C08F 32/08; C08F 30/04; C08F 30/08; C08F 30/10
[52] U.S. Cl. ..................... 526/308; 526/240; 526/279; 526/280; 526/281; 526/283; 526/347
[58] Field of Search ................................... 526/241, 308, 526/279, 280, 240, 281

[56] References Cited

U.S. PATENT DOCUMENTS

| | | | |
|---|---|---|---|
| 3,079,428 | 2/1963 | Baer et al. | 260/486 |
| 3,927,144 | 12/1975 | Hayashi et al. | |
| 3,962,198 | 6/1976 | Wada et al. | |
| 4,140,843 | 2/1979 | Widmer et al. | |
| 5,169,818 | 12/1992 | Antberg et al. | 502/159 |
| 5,262,498 | 11/1993 | Antberg et al. | 526/241 |
| 5,399,636 | 3/1995 | Alt et al. | |
| 5,451,649 | 9/1995 | Zenk et al. | |
| 5,473,020 | 12/1995 | Peifer et al. | |
| 5,534,473 | 7/1996 | Welch et al. | |
| 5,571,880 | 11/1996 | Alt et al. | |
| 5,594,078 | 1/1997 | Welch et al. | |
| 5,627,118 | 5/1997 | Palackal et al. | |
| 5,668,230 | 9/1997 | Schertl et al. | |

OTHER PUBLICATIONS

"Friedel–Crafts Polymerization of Fluorene with Methylene Chloride, Methoxyacetyl Chloride, and Chloromethyl Ether," Nystuen and Jones, Journal of Polymer Science: Polymer Chemistry Edition, vol. 23, 1433–1444 (1985).

"Synthesis of Vinylfluorene–Vinylfluorenone Polymers," Gipstein et al., Journal of Polymer Chemistry, Polymer Letters, vol. 9, 671–676 (1971).

*Primary Examiner*—Fred Zitomer
*Attorney, Agent, or Firm*—Edward L. Bowman

[57] ABSTRACT

Polymeric ligands, polymeric metallocenes, and processes for preparing same are provided. The process for preparing polymeric metallocenes comprises reacting a polymeric ligand, a transition metal compound, and an alkali metal compound. In one embodiment, a process for preparing polymeric ligands comprises reacting at least one bridged cyclopentadienyl-type monomer and an initiator under polymerization conditions. In another embodiment, a polymeric ligand is represented by the formula $[Q']_n$, wherein Q' is a unit containing at least one bridged cyclopentadienyl-type group and wherein n is 1–5000. In another embodiment, a polymeric metallocene is represented by the formula $[Q''MX_m]_n$, wherein Q" is a unit containing at least one fluorenyl-type group, M is a transition metal, each X is individually a hydrocarbyl group containing 1 to 20 carbon atoms, an alkoxy group containing 1 to 12 carbon atoms, an aryloxy group containing 6 to 20 carbon atoms, a halide, or hydride, m is 2 or 3, and wherein n is 1–5000. Other aspects of the present invention include a catalyst system comprising the polymeric metallocene and an organoaluminoxane, a method for preparing same, and a polymerization process employing the catalyst system.

12 Claims, No Drawings

POLYMERIC LIGANDS, POLYMERIC METALLOCENES, CATALYST SYSTEMS, PREPARATION, AND USE

This application is a Division of application Ser. No. 08/339,537, filed Nov. 15, 1994, now U.S. Pat. No. 5,770,755.

The present invention relates to polymeric ligands, polymeric metallocenes, catalyst systems, processes for preparing same, and olefin polymerization processes.

BACKGROUND OF THE INVENTION

Metallocene catalysts have been used in homogeneous solution polymerizations. Attempts to use soluble metallocene catalysts in a slurry or particle form type polymerization are currently not commercially feasible. It has been observed that when such particle form polymerizations are carried out in the presence of a soluble metallocene catalyst, large amounts of polymeric material are formed on the surfaces of the polymerization vessel. This fouling produces an adverse effect on the heat transfer and also results in the need for periodic, if not continuous, cleaning of the reactor.

It would therefore be desirable to produce economical metallocene catalysts useful in polymerization processes free of reactor fouling.

For many applications, such as thermoforming, extrusion, blow molding and the production of film, it is desirable to produce a polymer having a broad molecular weight distribution.

It would therefore be desirable to produce metallocene catalysts capable of producing polymers having a broad molecular weight distribution.

Another important characteristic of polymers is the environmental stress crack resistance, which can be improved by the incorporation of comonomer in the high molecular weight portion of polymers having a broad molecular weight distribution.

SUMMARY OF THE INVENTION

An object of the present invention is to provide a polymeric ligand useful in preparing polymeric metallocenes.

Another object of the present invention is to provide an economical process for preparing a polymeric ligand.

Another object of the present invention is to provide a polymeric metallocene useful in olefin polymerization which does not produce significant reactor fouling in a particle form polymerization process.

Another object of the present invention is to provide mixtures of polymeric metallocenes useful in preparing polymers having a broad molecular weight distribution.

Another object of the present invention is to provide mixtures of polymeric metallocenes useful in preparing polymers having improved environmental stress crack resistance.

Another object of the present invention is to provide an efficient and economical process for preparing polymeric metallocene catalysts.

Still another object of the present invention is to provide a polymerization process free of significant reactor fouling, especially in particle form processes.

In accordance with the present invention, polymeric ligands, polymeric metallocenes, catalyst systems, processes for preparing same, and polymerization processes are provided. The process for preparing polymeric metallocenes comprises reacting a polymeric ligand, an alkali metal compound, and a transition metal-containing compound, wherein the polymeric ligand contains a cyclopentadienyl-type group, as hereinafter defined, wherein the transition metal-containing compound is represented by the formula $MX_4$ wherein M is a transition metal, and each X is individually a hydrocarbyl group containing 1 to 20 carbon atoms, an alkoxy group containing 1 to 12 carbon atoms, an aryloxy group containing 6 to 20 carbon atoms, a halide, or hydride. In another embodiment, a process for preparing polymeric ligands comprises reacting at least one bridged cyclopentadienyl-type monomer, as hereinafter defined, and an initiator under polymerization conditions. In another embodiment, polymeric ligands are represented by the formula $[Q']_n$, wherein Q' is a unit containing at least one bridged cyclopentadienyl-type group and wherein n is 1–5000. Polymeric ligands comprising mixtures of bridged and unbridged cyclopentadienyl-type groups are also provided. In another embodiment, polymeric metallocenes are represented by the formula $[Q''MX_m]_n$, wherein Q'' is a unit containing at least one fluorenyl-type group, as hereinafter defined, M is a transition metal, each X is individually a hydrocarbyl group containing 1 to 20 carbon atoms, an alkoxy group containing 1 to 12 carbon atoms, an aryloxy group containing 6 to 20 carbon atoms, a halide, or hydride, m is 2 or 3, and wherein n is 1–5000. The catalyst systems comprise the polymeric metallocene and an organoaluminoxane. The polymerization process comprises contacting the catalyst system and at least one olefin under polymerization conditions.

DETAILED DESCRIPTION OF THE INVENTION

A process for preparing polymeric metallocenes comprises reacting a polymeric ligand, an alkali metal compound, and a transition metal-containing compound.

POLYMERIC LIGAND

The polymeric ligand employed in preparing the polymeric metallocene is represented by the formula $[Q]_n$, wherein Q is a unit containing at least one cyclopentadienyl-type group and wherein n is 1–5000, preferably 3–1000. Cyclopentadienyl-type, as used herein, includes groups containing a cyclopentadienyl functionality, and includes cyclopentadienyl, substituted cyclopentadienyl, indenyl, substituted indenyl, fluorenyl and substituted fluorenyl groups. Fluorenyl-type groups are preferred. Fluorenyl-type as used herein includes groups containing a fluorenyl functionality, and includes fluorenyl and substituted fluorenyl containing compounds. Typical substituents for the above defined cyclopentadienyl-type groups include hydrocarbyl groups containing 1 to 20 carbon atoms, preferably 1 to 12 carbon atoms, alkoxy groups containing 1 to 12 carbon atoms, or halide. Preferably the substituents are alkyl groups containing 1 to 10 carbon atoms, more preferably 1 to 6 carbon atoms. Some examples of substituents include methyl, ethyl, propyl, butyl, tert-butyl, isobutyl, amyl, isoamyl, hexyl, cyclohexyl, heptyl, octyl, nonyl, decyl, dodecyl, 2-ethylhexyl, pentenyl, butenyl, phenyl, chloride, bromide, and iodide.

Examples of typical cyclopentadienyl-type groups include fluorene, vinylcyclopentadiene, (1-methylethenyl) cyclopentadiene, (1-(4-vinyl)phenyl)cyclopentadiene, penta-2,4-dienylcyclopentadiene, 2-vinyl-7-methylfluorene, 1-vinyl-3-butylcyclopentadiene, 2,7-dimethyl-9-vinylfluorene, 1-vinylindene, 2-vinylindene, 3-vinylindene, 4-vinylindene, 5-vinylindene, 6-vinylindene, 7-vinylindene, 1-vinylfluorene, 2-vinylfluorene, 3-vinylfluorene, 4-vinylfluorene, 5-vinylfluorene, 6-vinylfluorene, 7-vinylfluorene, 8-vinylfluorene, 9-vinylfluorene, and mixtures thereof.

The term polymeric, as used herein, is intended to include both homopolymers and copolymers. Copolymers can include mixtures of cyclopentadienyl-type groups and/or other polymerizable monomers. The term polymerization, as used herein, is intended to include both homopolymerization and copolymerization. The term monomer, as used herein, refers to a compound capable of undergoing polymerization.

In addition to the at least one cyclopentadienyl-type group, the unit Q can also contain other groups, such as styrene. When styrene is employed, the relative amount of styrene and cyclopentadienyl-type group can vary broadly depending on the particular results desired. Generally, when employing a styrene comonomer, the styrene will be present in an amount in the range of from about 0.1 mole to about 5000 moles styrene per mole of cyclopentadienyl-type group, preferably styrene is present in the range of from about 0.1 mole to about 1500 moles styrene per mole cyclopentadienyl-type group, and more preferably from 1 mole to 1000 moles styrene per mole cyclopentadienyl-type group.

The polymeric ligands can be prepared by any method known in the art. Examples of some such methods are disclosed in U.S. Pat. No. 3,079,428, Journal of Polymer Science: Polymer Chemistry Edition, Vol. 23, 1433–1444 (1985), and Journal of Polymer Science, Polymer letters, Vol. 9, 671–676 (1971), the disclosures of which are incorporated herein by reference.

One method for preparing the polymeric ligand involves radical polymerization by reacting an initiator and at least one cyclopentadienyl-type monomer under polymerization conditions. Suitable initiators include azobisisobutyronitrile, phenyl-azo-triphenylmethane, tert-butyl peroxide, cumyl peroxide, acetyl peroxide, benzoyl peroxide, lauroyl peroxide, tert-butyl hydroperoxide, and tert-butyl perbenzoate. The method is also effective when employing styrene as comonomer. Generally the reaction is conducted in the presence of a diluent such as toluene. Generally conditions suitable for the radical polymerization of the cyclopentadienyl-type monomer will include a temperature in the range of from about 0° C. to about 150° C.

Another method for preparing the polymeric ligands involves cationic polymerization by reacting an initiator, such as boron trifluoride etherate, and a cyclopentadienyl-type monomer under polymerization conditions. Generally the reaction is conducted in a diluent such as methylene chloride. The method is also effective when employing styrene as comonomer. Suitable cationic polymerization conditions for preparing the polymeric ligand include a temperature in the range of from about −80° C. to about 0° C.

Still another method for preparing the polymeric ligands involves alkylating polymerization by reacting zinc dichloride or aluminum trichloride and a cyclopentadienyl-type monomer in chloromethyl methyl ether under polymerization conditions. Suitable alkylating polymerization conditions for preparing the polymeric ligand include a temperature in the range of from about −20° C. to about 50° C.

Another method for preparing the polymeric ligands involves anionic polymerization by reacting an alkali metal compound and a cyclopentadienyl-type monomer under polymerization conditions. Generally the reaction will be conducted in a diluent such as diethyl ether. Suitable conditions for anionic polymerization include a temperature in the range of from about 0° C. to about 150° C., preferably from about 0° C. to about 100° C., and more preferably from 0° C. to 50° C.

Alkali metal compounds suitable for preparing the polymeric ligand by anionic polymerization are represented by the formula AR', wherein A is an alkali metal selected from the group consisting of lithium, sodium, and potassium and wherein R' is a hydrocarbyl group selected from the group consisting of alkyl, cycloalkyl, and aryl groups containing 1 to 12 carbon atoms. Preferably R' is an alkyl group containing 1 to 10 carbon atoms. Lithium alkyls containing 1 to 8 carbon atoms are especially preferred. Examples of preferred lithium alkyls include methyllithium, ethyllithium, propyllithium, butyllithium, pentyllithium and hexyllithium. Excellent results have been obtained with n-butyllithium and it is especially preferred. The alkali metal compound is generally present in an amount in the range of from about 0.1 mole to about 20 moles alkali metal compound per mole cyclopentadienyl-type monomer, preferably about 0.2 mole to about 10 moles, and more preferably about 0.5 moles to about 5 moles alkali metal compound per mole cyclopentadienyl-type monomer.

BRIDGED POLYMERIC LIGAND

In one embodiment of the invention, a bridged polymeric ligand is provided. The bridged polymeric ligand is represented by the formula $(Q')_n$, wherein $Q'$ is a unit containing at least one bridged cyclopentadienyl-type group and wherein n is 1 to 5000, preferably 3–1000. The bridged cyclopentadienyl-type group is represented by the formula ZRZ, wherein each Z is individually a cyclopentadienyl-type group, and R is a bridging group and is an alkylene group containing from 1 to 12 carbon atoms, an aryl-containing group having from 6 to 12 carbon atoms, silicon-containing group, germanium-containing group, or tin-containing group. Preferably R is an alkylene group containing 1 to 10 carbon atoms.

Typical examples of bridged cyclopentadienyl-type monomers are
1-(9-(2-vinyl)fluorenyl)-2-(9-fluorenyl)ethane,
(9-(2-vinyl)fluorenyl)(cyclopentadienyl)methane,
(9-fluorenyl)(cyclopentadienyl)methane,
1-(9-(2-vinyl)fluorenyl)-2-(cyclopentadienyl)ethane,
(9-(2-vinyl)fluorenyl)(1-indenyl)methane,
1-(9-(2-vinyl)fluorenyl)-1-(cyclopentadienyl)cyclopentane,
(9-(2-vinyl)fluorenyl)(cyclopentadienyl)(1-cyclo-3-hexenyl)methane,
(9-(2-vinyl)fluorenyl)(cyclopentadienyl)dimethylmethane,
(9-fluorenyl)[1-(3-vinyl)phenylcyclopentadieyl]diphenylmethane,
(9-(2, 7-divinyl)fluorenyl)(1-(3-methyl)cyclopentadienyl)dimethylmethane,
(9-(2-vinyl)fluorenyl)(cyclopentadienyl)silane,
(9-(2-vinyl)fluorenyl)(cyclopentadienyl)dimethysilane,
(9-(2-vinyl)fluorenyl)(9-fluorenyl)diphenysilane,
(9-(2-vinyl)fluorenyl)(cyclopentadienyl)dimethylgermane,
(9-(2-vinyl)fluorenyl)(fluorenyl)dimethylstannane,
1-(9-(2-vinyl)fluorenyl)-3-(cyclopentadienyl)propane,
1-(9-fluorenyl)-1-(methyl)-1-(1-(2-vinylcyclopentadienyl)ethane,
(9-(2,7-diphenylfluorenyl)(1-(3-vinyl)cyclopentadienyl)diphenylmethane,
bis(9-(1-methyl-4-vinyl)fluorenyl)diphenylmethane,
bis(9-fluorenyl)dimethylmethane, (fluorenyl)(cyclopentadienyl)methyl))1-(4-vinyl) phenyl)methane and mixtures thereof.

The method for preparing the bridged polymeric ligand comprises reacting at least one bridged cyclopentadienyl-type monomer and an initiator compound under polymerization conditions.

The bridged cyclopentadienyl-type monomers can be prepared by any method known in the art. Examples of such methods are disclosed in Stone et al. in J. Org. Chem., 49, 1849 (1984), European Published Application 524,624, and U.S. Pat. Nos. 5,191,132 and 5,347,026, the disclosures of which are incorporated herein by reference.

One method for preparing bridged cyclopentadienyl-type monomers involves reacting a cyclopentadienyl-type compound with an alkali metal compound, and then with a halogenated cyclopentadienyl-type compound. The halogenated cyclopentadienyl-type compound can be prepared by reacting a lithiated cyclopentadienyl-type compound and an organo halide, such as dibromoethane or dichloromethane.

Alkali metal compounds suitable for preparing the bridged cyclopentadienyl-type monomer include those defined above for preparing the polymeric ligand. Lithium alkyls containing 1 to 8 carbon atoms are preferred. Excellent results have been obtained with n-butyllithium and it is especially preferred. When preparing the bridged cyclopentadienyl-type monomer, the alkali metal compound is generally present in an amount in the range of from about 0.1 mole to about 20 moles alkali metal compound per mole cyclopentadienyl-type compound, preferably about 0.2 mole to about 10 moles, and more preferably about 0.5 moles to about 5 moles alkali metal compound per mole cyclopentadienyl-type compound.

Reaction conditions for reacting the cyclopentadienyl-type compound and the alkali metal compound to produce the bridged cyclopentadienyl-type monomer include a temperature in the range of from about 0° C. to about 150° C., preferably from about 0° C. to about 100° C., and more preferably from 0° C. to 50° C.

The at least one bridged cyclopentadienyl-type monomer is reacted with a suitable initiator compound under polymerization conditions to prepare the bridged polymeric ligand. Suitable initiator compounds include azobisisobutyronitrile, phenyl-azo-triphenylmethane, tert-butyl peroxide, cumyl peroxide, acetyl peroxide, benzoyl peroxide, lauroyl peroxide, tert-butyl hydroperoxide, tert-butyl perbenzoate, boron trifluoride etherate, alkali metal compounds, zinc dichloride, and aluminum trichloride. Suitable alkali metal compounds include those described above for preparing the bridged cyclopentadienyl-type monomers.

Typically the reaction is conducted in diluents similar to those described above for radical, cationic, alkylating, and anionic polymerizations. As noted above, typical examples of such diluents include toluene, methylene chloride, chloromethyl methyl ether, and diethyl ether for the respective polymerization.

When preparing polymeric ligands containing at least one bridged cyclopentadienyl-type group, the initiator is generally present in an amount in the range of from about 0.0001 mole to about 20 moles initiator per mole cyclopentadienyl-type monomer, preferably about 0.001 mole to about 10 moles, and more preferably about 0.005 moles to about 5 moles initiator per mole cyclopentadienyl-type monomer.

Conditions for preparing the polymeric ligand containing at least one bridged cyclopentadienyl-type group vary broadly depending on the reactants employed. Generally the temperature is in the range of from about −80° C. to about 150° C. Suitable conditions are similar to those disclosed above for radical, cationic, alkylating, and anionic polymerizations.

The method is also suitable for the copolymerization of mixtures of bridged and unbridged cyclopentadienyl-type monomers. The term "unbridged" as used herein refers to groups which are not connected by a bridging group. The mixtures can be selected so as to prepare catalyst systems capable of producing polymers having a broad molecular weight distribution and good environmental stress crack resistance. When polymerizing mixtures of bridged and unbridged cyclopentadienyl-type groups, typically the bridged cyclopentadienyl-type group will be present in an amount in the range of from about 0.001 mole to about 1000 moles per mole of unbridged cyclopentadienyl-type group, preferably from about 0.01 mole to about 100 moles per mole of unbridged cyclopentadienyl-type group.

The method is also suitable for the copolymerization of at least one bridged cyclopentadienyl-type monomer with styrene or other similar conjugated system. When employing a styrene comonomer, good results have been obtained when employing azobisisobutyronitrile as initiator and toluene as diluent.

POLYMERIC METALLOCENES

The process for preparing polymeric metallocenes comprises reacting the polymeric ligand, an alkali metal compound, and a transition metal-containing compound.

The polymeric ligand contains a cyclopentadienyl-type group and can be prepared by any method described above.

The transition metal-containing compound is represented by the formula $MX_4$, wherein M is a Group IVB or VB transition metal, preferably M is zirconium, hafnium, titanium, or vanadium, more preferably zirconium, hafnium, or titanium, and wherein each X is individually a hydrocarbyl group containing 1 to 20 carbon atoms, preferably 1 to 16 carbon atoms, an alkoxy group containing 1 to 12 carbon atoms, preferably 1 to 8 carbon atoms, an aryloxy group containing 6 to 20 carbon atoms, preferably 6 to 12 carbon atoms, a halide, preferably chloride, or hydride. Preferably X is a halide or a cyclopentadienyl-type group.

Alkali metal compounds suitable for preparing the polymeric metallocene include those defined above for preparing the polymeric ligand. Lithium alkyls containing 1 to 8 carbon atoms are preferred. Excellent results have been obtained with n-butyllithium and it is especially preferred.

In preparing the polymeric metallocene, the alkali metal compound is generally present in an amount in the range of from about 0.1 mole to about 20 moles alkali metal compound per mole cyclopentadienyl-type group, preferably about 0.2 mole to about 10 moles, and more preferably about 0.2 moles to about 5 moles alkali metal compound per mole cyclopentadienyl-type group.

Suitable transition metal-containing compounds for preparing the polymeric metallocene include titanium tetrachloride, zirconium tetrachloride, hafnium tetrachloride, vanadium tetrachloride, titanium tetrabromide, zirconium tetrabromide, hafnium tetrabromide, vanadium tetrabromide, titanium tetraiodide, zirconium tetrabromide, hafnium tetrabromide, vanadium tetrabromide, zirconium tetramethoxide, titanium tetramethoxide, hafnium tetramethoxide, vanadium tetramethoxide, zirconium tetraethoxide, titanium tetraethoxide, hafnium tetraethoxide, vanadium tetraethoxide, cyclopentadienylzirconium trichloride, cyclopentadienyltitanium trichloride, cyclopentadienylhafnium trichloride, cyclopentadienylvanadium trichloride, pentamethylcyclopentadienylzirconium trichloride, pentamethylcyclopentadienyltitanium trichloride, pentamethylcyclopentadienylhafnium trichloride, pentamethylcyclopentadienylvanadium trichloride, indenylzirconium trichloride, and idenyltitanium trichloride. Zirconium-containing and titanium-containing compounds are preferred and zirconium tetrachloride and cyclopentadienylzirconium trichloride are especially preferred.

In preparing the polymeric metallocene, the transition metal-containing compound is generally present in an amount in the range of from about 0.1 mole to about 20 moles transition metal-containing compound per mole cyclopentadienyl-type group, preferably about 0.2 mole to about 10 moles, and more preferably about 0.5 moles to about 5 moles per mole cyclopentadienyl-type group.

The polymeric ligand, the alkali metal compound, and the transition metal-containing compound are generally reacted at a temperature in the range of from about −80° C. to about 150° C., preferably from about −40° C. to about 100° C., and more preferably from 0° C. to 50° C.

Preferably the polymeric ligand and the alkali metal compound are contacted first, prior to contacting with the transition metal-containing compound. Typically the reactions will be conducted in a diluent such as tetrahydrofuran, pentane, or diethylether.

In another embodiment, polymeric metallocenes are represented by the formula $[Q"MX_m]_n$, wherein Q" is a unit containing at least one fluorenyl-type group, M is a transition metal, each X is individually a hydrocarbyl group containing 1 to 20 carbon atoms, an alkoxy group containing 1 to 12 carbon atoms, an aryloxy group containing 6 to 20 carbon atoms, a halide, or hydride, m is 2 or 3, and wherein n is 1–5000, preferably 3–1000. Preferably X is a halide or a cyclopentadienyl-type group.

Catalyst Systems

The polymeric metallocenes can be used in combination with a suitable cocatalyst to produce catalyst systems for the polymerization of olefins. Examples of suitable cocatalysts include any of those organometallic cocatalysts which have in the past been employed in conjunction with transition metal-containing olefin polymerization catalysts. Some typical examples include organometallic compounds of metals of Groups IA, IIA, and IIIB of the Periodic Table. Examples of such compounds include organometallic halide compounds, organometallic hydrides, and metal hydrides. Some specific examples include triethylaluminum, triisobutylaluminum, diethylaluminum chloride, diethylaluminum hydride, and the like. Other examples of known cocatalysts include the use of compounds capable of forming a stable non-coordinating counter anion, such as disclosed in U.S. Pat. No. 5,155,080, e.g. using triphenyl carbenium tetrakis(pentafluorophenyl)boronate or tris(pentaflurophenyl)boron. Another example would be the use of a mixture of trimethylaluminum and dimethylfluoroaluminum such as disclosed by Zambelli et, *Macromolecules*, 22, 2186 (1989).

Currently, organoaluminoxane cocatalysts are the preferred cocatalysts. Various techniques are known for making organoaluminoxanes. One technique involves the controlled addition of water to a trialkylaluminum. Another technique involves combining a trialkylaluminum and a hydrocarbon with a compound containing water of adsorption or a salt containing water of crystallization. Many suitable organoaluminoxanes are commercially available.

Typically the organoaluminoxanes comprise oligomeric, linear and/or cyclic hydrocarbyl aluminoxanes having repeating units of the formula

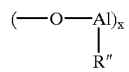

wherein each R" is a hydrocarbyl group, preferably an alkyl group containing 1–8 carbon atoms, x is 2 to 50, preferably 4 to 40, and more preferably 10 to 40. Typically R" is predominantly methyl or ethyl. Preferably at least about 30 mole percent of the repeating groups have an R which is methyl, more preferably at least 50 mole percent, and still more preferably at least 70 mole percent. Generally in the preparation of an organoaluminoxane, a mixture of linear and cyclic compounds is obtained. Organoaluminoxanes are commercially available in the form of hydrocarbon solutions, generally aromatic hydrocarbon solutions.

An organoaluminoxy product can be prepared by reacting an organoaluminoxane and an oxygen-containing compound selected from the group consisting of organo boroxines, organic boranes, organic peroxides, alkylene oxides, and organic carbonates. Organo boroxines are preferred. One such method is disclosed in U.S. Pat. No. 5,354,721, the disclosure of which is incorporated herein by reference.

The amount of organoaluminoxane relative to the polymeric metallocene employed in the catalyst system can vary broadly depending upon the particular catalyst selected and the results desired. Typically, the organoaluminoxane is present in the amount of about 0.5 moles to about 10,000 moles aluminum per mole of metal in the polymeric metallocene, preferably about 10 moles to about 5,000 moles, and more preferably 50 moles to 5,000 moles.

The polymeric metallocene and the cocatalyst are generally contacted in the presence of a solvent or a diluent. Typical diluents include, for example, toluene, tetrahydrofuran, dichloromethane, heptane, hexane, benzene, and diethylether.

Polymerization Processes

A variety of olefin compounds are suitable for use as monomers in the polymerization process of the present invention. Olefins which can be employed include linear, branched, and cyclic aliphatic olefins. While the invention would appear to be suitable for use with any aliphatic olefin known to be employed with metallocenes, those olefins having 2 to 18 carbon atoms are most often used. Ethylene and propylene are especially preferred. Often a second or third olefin (comonomer) having from 2 to 12 carbon atoms, preferably from 4 to 10 carbon atoms can be employed. Typical comonomers include propylene, 1-butene, 3-methyl-1-butene, 1-pentene, 4-methyl-1-pentene, 2-pentene, 1-hexene, 2-hexene, cyclohexene, 1-heptene, and dienes such as butadiene. Of these, 1-hexene is preferred.

The polymerization processes according to the present invention can be performed either batchwise or continuously. The olefin, polymeric metallocene, and organoaluminoxane cocatalyst can be contacted in any order. It is preferred that the polymeric metallocene and the organoaluminoxane are contacted prior to contacting with the olefin. It may be advantageous to dry the reaction product before contacting with the olefin. Generally a diluent such as isobutane is added to the reactor. The reactor is heated to the desired reaction temperature and olefin, such as ethylene or propylene, is then admitted and maintained at a partial pressure within a range of from about 0.5 MPa to about 5.0 MPa (70–725 psi) for best results. At the end of the designated reaction period, the polymerization reaction is terminated and the unreacted olefin and diluent vented. The reactor can be opened and the polymer can be collected as a free-flowing white solid and dried to obtain the product.

The reaction conditions for contacting the olefin and the catalyst system can vary broadly depending on the olefin employed, and are those sufficient to polymerize the olefins. Generally the temperature is in the range of about 20° C. to about 300° C., preferably in the range of 50° C. to 110° C. The pressure is generally in the range of from about 0.5 MPa to about 5.0 MPa (70–725 psi).

The present invention is particularly useful in a gas phase particle form or slurry type polynerization. A particularly preferred type particle form polymerization involves a continuous loop reactor which is continuously charged with suitable quantities of diluent, catalyst system, and polymerizable compounds in any desirable order. Typically the polymerization will include a higher alpha-olefin comonomer and optionally hydrogen. Generally the particle form polymerization is conducted at a temperature in the range of about 50° C. to about 110° C., although higher and lower temperatures can be used. The reaction product can be continuously withdrawn and the polymer recovered as appropriate, generally by flashing the diluent and unreacted monomers and drying the resulting polymer.

The olefin polymers made with the present invention are useful in preparing articles prepared by conventional polyolefin processing techniques, such as injection molding, rotational molding, extrusion of film, pipe extrusion, and blow molding.

The following examples serve to show the present invention in detail by way of illustration and not by way of limitation.

EXAMPLES

Examples 1–4 present inventive polymeric ligands, polymeric metallocenes, catalyst systems, and their preparation.

Examples 5–6 demonstrate the effectiveness of the inventive polymeric metallocenes in catalyst systems for the polymerization of olefins.

Example 1

Synthesis of 2-vinylfluorene

In the following examples, the general procedure described by K. Wong, in Polym. Bul. 1982, 8, 411 for preparing 2-vinylfluorene was followed. In 400 mL ethanol, 46.8 g (0.23 mol) 2-acetylfluorene, (prepared as described in Chem. Abstr. 1965, 62:6443h, also available from Aldrich Chemical Co., Inc., Milwaukee, Wis. 53233) and 8.70 g (0.23 mol) sodium borohydride were refluxed for 2 hours. Then the reaction mixture was concentrated by evaporation under vacuum. The residue was taken up in 300 mL diethyl ether and washed three times with 250 mL water. The organic phase was dried over sodium sulfate and concentrated by evaporation under vacuum. The yield was 45.9 g 2-(1-hydroxyethyl)fluorene (97%) in the form of a slightly yellow solid. Then 45.8 g (0.22 mol) 2-(1-hydroxyethyl) fluorene and 2.10 g (0.011 mol) p-toluenesulfonyl chloride in 600 mL toluene were refluxed for 3 hours. The solvent was evaporated under vacuum, the residue was filtered with pentane on alumina B and silica gel 60 and brought to −30° for crystallization. The thus prepared 2-vinylfluorene precipitated as a white, crystalline solid. The yield was 16.9 g of 2-vinylfluorene (40%).

Polymeric Ligand A

Radical polymerization of 2-vinylfluorene

To 3.00 g (15.6 mmol) 2-vinylfluorene in 16 mmL toluene, 0.13 g (0.8 mmol) of azobisisobutyronitrile (AIBN) was added with stirring. The reaction continued for 3 days at 90° C. The toluene soluble polymer was precipitated with cold methanol. The thus produced polymeric ligand was then purified by double reprecipitation from benzene and dried overnight at room temperature under vacuum. The yield was 60–70% of polymeric ligand A. Polymeric ligand A was employed in preparing the polymeric metallocene AA.

Polymeric Ligands B–F

Radical Copolymerization of 2-vinylfluorene and styrene

Reaction mixtures of 2-vinylfluorene and styrene were stirred with AIBN in solution in toluene for 3 days at 90° C. The relative ratios of 2-vinylfluorene to styrene were 1:1, 1:10, 1:20, 1:50, and 1:100, polymeric ligands B-F respectively. A typical example of the polymerizations was conducted by reacting 1.92 g (10 mmol) 2-vinyl fluorene, 10.42 g (100 mmol) styrene, and 0.90 g (5.5 mmol) AIBN in 110 mL toluene for 3 days at 90° C. The toluene soluble polymers were precipitated with cold methanol. The thus produced polymeric ligands were then purified by double reprecipitation from benzene and dried overnight at room temperature under vacuum. The yield was 40–70% of polymeric ligands B, C, D, E, and F. The polymeric ligands B–F were employed in preparing polymeric metallocenes BB, CC, DD, EE, and FF respectively.

In the table below:

Ligand is the polymeric ligand.

Fluorene/Styrene employed is the molar ratio of 2-vinylfluorene to styrene employed.

Fluorene/Styrene composition is the molar ratio of fluorene to styrene in the final polymeric composition.

$M_n$ is the number average molecular weight of the polymeric ligand.

$M_w$ is the weight average molecular weight of the polymeric ligand.

TABLE 1

| Ligand | Fluorene/ Styrene employed | Fluorene/ Styrene composition | $M_n$ | $M_w$ |
|---|---|---|---|---|
| A | 1:0 | 1:0 | 3000 | 9400 |
| B | 1:1 | 1:1.1 | 3500 | 15200 |
| C | 1:10 | 1:16 | 6200 | 16200 |
| D | 1:20 | 1:28.6 | 3300 | 5800 |
| E | 1:50 | 1:45.6 | 6500 | 13600 |
| F | 1:100 | 1:86.2 | 6700 | 21200 |

Polymeric Metallocenes AA–FF

The above prepared polymeric ligands A–F were individually suspended in pentane and mixed with an equimolar quantity of n-butyllithium (1.6M in hexane). The mixtures were stirred for 24 hours at room temperature. The supernatant was decanted, and each polymer was washed three times with 50 mL of pentane. Each washed polymer was combined with 50 mL pentane and an equimolar quantity of cyclopentadienylzirconium trichloride. Each reaction mixture was stirred for 24 hours at room temperature and the supernatant was then decanted. The thus produced polymeric metallocenes AA–FF were washed three times with 50 mL pentane and dried overnight at room temperature under vacuum.

Example 2

Polymeric Ligand G

Alkylating Polymerization of fluorene

To 10.00 g (0.06 mol) fluorene dissolved in 40 mL (0.53 mol) chloromethyl methyl ether, 32.72 g (0.24 mol) zinc(II) chloride was added with cooling in ice. The suspension was stirred for 30 minutes at room temperature. The mixture was slowly poured into 200 mL 10% KOH in methanol. The supernatant was decanted and the precipitated polyfluorene was washed five times with 100 mL methanol in water. The residue was stirred two times for 1 hour in 100 mL acetone. Upon filtering, a yellow-beige colored powder was recovered and then dried under vacuum at room temperature. The yield was 58% of polymeric ligand G which was employed in preparing the polymeric metallocene GG.

Polymeric Metallocene GG

To 1.20 g of the above prepared polymeric ligand G in 30 mL diethyl ether, was added 5.0 mL (8.0 mmol) n-butyllithium (1.6 M in hexane) with stirring. The reaction mixture was stirred overnight at room temperature. The supernatant was decanted and the thus produced polymeric ligand was washed three times with 30 mL diethyl ether. Then the polymeric ligand was combined with 40 mL diethyl ether and 1.50 g (5.7 mrnmol) cyclopentadienylzirconium trichloride. The reaction mixture was stirred for 24 hours at room temperature. The supernatant was decanted and the polymeric metallocene GG was washed three times with 30 mL diethyl ether and dried overnight at room temperature under high vacuum.

Example 3

Synthesis of the Bridged Monomer 1-(9-(2-vinylfluorenyl)-2-(9-fluorenyl)ethane To 1.15 g (6.0 mmol) 2-vinylfluorene in 100 mL diethyl ether was added 3.75 mL (6.0 mmol) n-butyllithium (1.6M in hexane). The reaction mixture was stirred for 4 hours at room temperature. Then 1.64 g (6.0 mmol) 1-bromo-2-(9-fluorenyl)ethane was added and the mixture was stirred for 14 hours at room temperature. The precipitate was removed by filtration, washed with methanol, filtered with pentane using silica gel 60, and concentrated by evaporation under vacuum. The yield was 1.69 g (73%) 1-(9-(2-vinyl) fluorenyl)-2-(9-fluorenyl)ethane as a colorless solid.

Bridged Polymeric Ligand H

Poly[1-(9-(2-vinyl)fluorenyl)-2-(9-fluorenyl)ethane]

To 0.31 g (2.1 mmol) 1-(9-(2-vinyl)fluorenyl)-2-(9-fluorenyl)ethane in 50 mL diethyl ether, was added 2.63 mL (4.2 mmol) n-butyllithium (1.6M in hexane). The reaction mixture was stirred overnight at room temperature to produce the polymeric ligand H which was employed in the polymerization of the polymeric metallocene HH.

Polymeric Metallocene HH

Poly[1-(9-(2-vinyl)fluorenyl)-2-(9-fluorenyl)ethane zirconium dichloride]

To the reaction mixture containing polymeric ligand H was added 0.49 g zirconium tetrachloride. The mixture was stirred overnight at room temperature. The solvent was removed by evaporation under vacuum. The thus produced red solid poly[1-( 9-(2-vinyl)fluorenyl)-2-(9-fluorenyl) ethane zirconium dichloride] was extracted with methylene chloride, and then the solvent was removed by evaporation under vacuum to produce the polymeric metallocene HH.

Polymeric Ligand I

Copolymerization of 1-(9-(2-vinyl)fluorenyl)-2-(9-fluorenyl)ethane and Styrene

The following compounds were combined in 17 mL toluene and stirred for 3 days at 90° C.; 0.30 g (0.8 mmol) 1-(9-(2-vinyl)iluorenyl)-2-(9-fluorenyl)ethane, 1.84 mL styrene, and 0.14 g (0.84 mmol) AIBN. The toluene-soluble copolymer was precipitated in cold methanol, purified by double reprecipitation form benzene and dried at room temperature under vacuum. The yield was 40–50 % polymeric ligand poly[styrene/1-(9-(2-vinyl)fluorenyl)-2-(9-fluorenyl)ethane]. In the Table below:

Ligand is the polymeric ligand.

Fluorene/Styrene employed is the molar ratio of 2-vinylfluorene to styrene employed.

Fluorene/Styrene composition is the molar ratio of fluorene to styrene in the final polymeric composition.

$M_n$ is the number average molecular weight of the polymeric ligand.

$M_w$ is the weight average molecular weight of the polymeric ligand.

TABLE 2

| Ligand | Fluorene/Styrene employed | Fluorene/Styrene composition | $M_n$ | $M_w$ |
|---|---|---|---|---|
| I | 1:20 | 1:26.4 | 1700 | 5100 |

Polymeric Metallocene 11

Synthesis of Poly[styrene/1-(9-(2-vinyl)fluorenyl)-2-(9-fluorenyl)ethane Zirconium Dichloride]

To 0.70 g (0.8 mmol) styrene/1-(9-(2-vinyl)fluorenyl)-2-(9-fluorenyl)ethane in 20 mL pentane was added 5.0 mL (0.8 mmol) n-butyllithium. The mixture was stirred for 24 hours at room temperature. The supernatant was decanted and the polymer washed three times with 30 mL pentane. Then 30 mL pentane and 0.70 g (3.0 mmol) zirconium tetrachloride. The reaction mixture was stirred overnight at room temperature. The supernatant was decanted and the orange polymer was washed three times with 30 mL pentane and dried at room temperature under vacuum. The yield was 1.08 g styrene/1-(9-(2-vinyl)fluorenyl)-2-(9-fluorenyl)ethane zirconium dichloride, polymeric metallocene II.

Example 4

Polymeric Ligands J–N

Cationic Polymerization of 2-vinylfluorene

At a temperature of −78° C., 1.92 g (10.0 mmol) 2-vinylfluorene in 30 mL methylene chloride and 0.60 mL (5.0 mmol) boron trifluoride etherate were combined. The mixture was stirred overnight at −30° C. The precipitated polymer was separated by filtration, dissolved in benzene, precipitated in cold methanol, reprecipitated from benzene, and dried overnight at room temperature under vacuum. The yield of polymeric ligand J was 70–80%.

Cationic copolymerization of 2-vinylfluorene and styrene

The 2-vinylfluorene and styrene were stirred overnight with 50 mol% boron trifluoride etherate in methylene chloride at −30° C. The polymers insoluble in methylene chloride were separated by filtration, dissolved in benzene, precipitated in cold methanol, purified by reprecipitation from benzene and dried under vacuum at room temperature. The yield of polymeric ligands K–N was 60–75%.

In the Table below:

Ligand is the polymeric ligand.

Fluorene/Styrene employed is the molar ratio of 2-vinylfluorene to styrene employed.

Fluorene/Styrene composition is the molar ratio of fluorene to styrene in the final polymeric composition.

$M_n$ is the number average molecular weight of the polymeric ligand.

$M_w$ is the weight average molecular weight of the polymeric ligand.

TABLE 3

| Ligand | Fluorene/ Styrene employed | Fluorene/ Styrene composition | $M_n$ | $M_w$ |
| --- | --- | --- | --- | --- |
| J | 1:0 | 1:0 | 5000 | 7900 |
| K | 1:1 | 1:1.2 | 4500 | 16400 |
| L | 1:10 | 1:3.8 | 8500 | 29300 |
| M | 1:50 | 1:11.1 | 9300 | 23100 |
| N | 1:100 | 1:33.2 | 11500 | 30700 |

Example 5

Polymerization of Ethylene

The polymeric metallocenes were individually suspended in toluene and activated by the addition of methylaluminoxane (MAO), 30 wt % in toluene, Mw=1100, WITCO) in a 1,000-fold excess.

The polymerizations were carried out in a one liter Buchi laboratory autoclave. The autoclave was charged with 500 mL pentane, 2 mL MAO, and the indicated polymeric metallocene. The reactor temperature was regulated at 60° C. and a constant pressure of 10 bar of ethylene was applied. After one hour, the polymerization reaction was interrupted, and the polyethylene was recovered and the yield determined. The results are summarized in Table 1.

In the Table below:

Metallocene is the polymeric metallocene in mg.

Polyethylene is the yield of polyethylene in grams.

Activity/M is the grams polyethylene per (gram polymeric metallocene•hour•bar).

Activity/Zr is the grams polyethylene per (gram zirconium•hour•bar).

TABLE 4

| Metallocene mg | Polyethylene g | Activity/M g PE/g M.hr.b | Activity/Zr g PE/g Zr.hr.b |
| --- | --- | --- | --- |
| AA 4 | 29.5 | 738 | 3400 |
| BB 2 | 14.5 | 725 | 4200 |
| CC 2 | 53.0 | 2650 | 61000 |
| DD 2 | 55.5 | 2775 | 103000 |
| EE 28 | 22.5 | 80 | 4600 |
| FF 104 | 16.0 | 15 | 1600 |
| GG 14 | 31.0 | 221 | 1100 |
| HH 1 | 34.5 | 3455 | 20600 |
| II 70 | 7.5 | 11 | 390 |

Example 6

Polymerization of Propylene

To a one liter Buchi autoclave was charged 2 mL MAO (30 wt % in toluene) and 500 mL propylene. The contents were stirred for 30 minutes at 20° C. in order to dry the propylene. To the autoclave was added 11.9 mg polymeric metallocene HH suspended in toluene and mixed with the appropriate quantity of MAO. The autoclave was regulated to 60° C. for one hour. The yield of polypropylene was 3.4 g and the activity of the metallocene was 285 g polypropylene/(g metallocene•hour).

That which is claimed is:

1. A process for preparing a polymeric ligand said process comprising contacting at least one bridged cyclopentadienyl-type monomer and at least one initiator under polymerization conditions wherein said polymeric ligand is represented by the formula $Q_n$, and wherein Q is a unit containing said at least one bridged cyclopentadienyl-type monomer, and wherein said polymeric ligand is a homopolymer or a copolymer, n is 1–5000, and wherein said at least one bridged cyclopentadienyl-type monomer is represented by the formula ZRZ wherein each Z is individually a cyclopentadienyl-type group selected from the group consisting of cyclopentadienyl, substituted cyclopentadienyl, indenyl, substituted indenyl, fluorenyl, substituted fluorenyl, styrene, and substituted styrene, R is a bridging group and is an alkylene group containing from 1 to 12 carbon atoms, an aryl-containing group having from 6 to 12 carbon atoms, silicon-containing group, germanium-containing group, or tin-containing group, and wherein said at least one initiator is selected from the group consisting of azobisisobutyronitrile, phenyl-azo-triphenylmethane, tert-butyl peroxide, cumyl peroxide, acetyl peroxide, benzoyl peroxide, lauroyl peroxide, tert-butyl hydroperoxide, tert-butyl perbenzoate, boron trifluoride etherate, alkali metal compounds, zinc dichloride, and aluminum trichloride.

2. A process according to claim 1 wherein at least one Z is fluorenyl or substituted fluorenyl.

3. A process according to claim 2 wherein said at least one initiator is selected from the group consisting of alkali metal compounds, azobisisobutyronitrile, zinc dichloride, or boron trifluoride etherate.

4. A process according to claim 3 wherein said at least one initiator is a lithium alkyl containing 1 to 8 carbon atoms.

5. A process for preparing a polymeric ligand said process comprising contacting at least one bridged cyclopentadienyl-type monomer, at least one unbridged cyclopentadienyl-type monomer and at least one initiator under polymerization conditions wherein said polymeric ligand is represented by the formula $Q_n$, and wherein Q is a unit containing said at least one bridged cyclopentadienyl-type monomer, and wherein said polymeric ligand is a copolymer, n is 1–5000, and wherein said at least one bridged cyclopentadienyl-type monomer is represented by the formula ZRZ wherein each Z is individually a cyclopentadienyl-type group selected from the group consisting of cyclopentadienyl, substituted cyclopentadienyl, indenyl, substituted indenyl, fluorenyl, substituted fluorenyl, styrene, and substituted styrene, R is a bridging group and is an alkylene group containing from 1 to 12 carbon atoms, an aryl-containing group having from 6 to 12 carbon atoms, silicon-containing group, germanium-containing group, or tin-containing group, and wherein said at least one unbridged cyclopentadienyl-type monomer is represented by the formula Z wherein Z is a cyclopentadienyl-type group selected from the group consisting of cyclopentadienyl, substituted cyclopentadienyl, indenyl, substituted indenyl, fluorenyl, substituted fluorenyl, styrene, and substituted styrene, and wherein said at least one initiator is selected from the group consisting of azobisisobutyronitrile, phenyl-azo-triphenylmethane, tert-butyl peroxide, cumyl peroxide, acetyl peroxide, benzoyl peroxide, lauroyl peroxide, tert-butyl hydroperoxide, tert-butyl perbenzoate, boron trifluoride etherate, alkali metal compounds, zinc dichloride, and aluminum trichloride.

6. A process according to claim 5 wherein at least one Z is fluorenyl or substituted fluorenyl and at least one Z is styrene or substituted styrene.

7. A process according to claim 6 wherein said at least one initiator is selected from the group consisting of alkali metal compounds, azobisisobutyronitrile, zinc dichloride, or boron trifluoride etherate.

8. A process according to claim 7 wherein said at least one initiator is a lithium alkyl containing 1 to 8 carbon atoms.

9. A process according to claim 1 wherein said bridged cyclopentadienyl-type monomers are selected from the group consisting of
1-(9-(2-vinyl)fluorenyl)-2-(9-fluorenyl)ethane,
(9-(2-vinyl)fluorenyl)(cyclopentadienyl)methane,
(9-fluorenyl)(cyclopentadienyl)methane,
1-(9-(2-vinyl)fluorenyl)-2-(cyclopentadienyl)ethane,
(9-(2-vinyl)fluorenyl)(1-indenyl)methane,
1-(9-(2-vinyl)fluorenyl)-1-(cyclopentadienyl)cyclopentane,
(9-(2-vinyl)fluorenyl)(cyclopentadienyl)(1-cyclo-3-hexenyl)methane,
(9-(2-vinyl)fluorenyl)(cyclopentadienyl)dimethylmethane,
(9-fluorenyl)[1-(3-vinyl)phenylcyclopentadienyl]diphenylmethane,
(9(2,7-divinyl)fluorenyl)(1-(3-methyl)cyclopentadienyl)dimethylmethane,
(9-(2-vinyl)fluorenyl)(cyclopentadienyl)silane,
(9-(2-vinyl)fluorenyl)(cyclopentadienyl)dimethylsilane,
(9-(2-vinyl)fluorenyl)(9-fluorenyl)diphenylsilane,
(9-(2-vinyl)fluorenyl)(cyclopentadienyl)dimethylgermane,
(9-(2-vinyl)fluorenyl)(fluorenyl)dimethylstannane,
1-(9-(2-vinyl)fluorenyl)-3-(cyclopentadienyl)propane,
1-(9-fluorenyl)-1-(methyl)-1-(1-(2-vinylcyclopentadienyl)ethane,
(9-(2,7-diphenylfluorenyl)(1-(3-vinyl)cyclopentadienyl)diphenylmethane,
bis(9-(1-methyl-4-vinyl)fluorenyl)diphenylmethane,
bis(9-fluorenyl)dimethylmethane, and
(fluorenyl)(cyclopentadienyl)methyl)(1-(4vinyl)phenyl)methane.

10. A process according to claim 5 wherein said bridged cyclopentadienyl-type monomers are selected from the group consisting of
1-(9-)2-vinyl)fluorenyl)-2-(9-fluorenyl)ethane,
(9-(2-vinyl)fluorenyl)(cycolpentadienyl)methane,
(9-fluorenyl)(cyclopentadienyl)methane,
1-(9-(2-vinyl)fluorenyl)-2-(cyclopentadienyl)ethane,
(9-(2-vinyl)fluorenyl)(1-indenyl)methane,
1-(9-(2-vinyl)fluorenyl)-1-(cyclopentadienyl)cyclopentane,
(9-(2-vinyl)fluorenyl)(cyclopentadienyl)(1-cyclo-3-hexenyl)methane,
(9-(2-vinyl)fluorenyl)(cyclopentadienyl)dimethylmethane,
(9-fluorenyl)[1-(3-vinyl)phenylcyclopentadienyl]diphenylmethane,
(9-(2,7-divinyl)fluorenyl)(1-(3-methyl)cyclopentadienyl)dimethylmethane,
(9-(2-vinyl)fluorenyl)(cyclopentadienyl)silane,
(9-(2-vinyl)fluorenyl)(cyclopentadienyl)dimethylsilane,
(9-(2-vinyl)fluorenyl)(9-fluorenyl)diphenylsilane,
(9-(2-vinyl)fluorenyl)(cyclopentadienyl)dimethylgermane,
(9-(2-vinyl)fluorenyl)(fluorenyl)dimethylstannane,
1-(9-(2-vinyl)fluorenyl)-3-(cyclopentadienyl)propane,
1-(9-fluorenyl)-1-(methyl)-1-(1-(2-vinylcyclopentadienyl)ethane,
(9-(2,7-diphenylfluorenyl)(1-(3-vinyl)cyclopentadienyl)diphenylmethane,
bis(9-(1-methyl-4-vinyl)fluorenyl)diphenylmethane,
bis(9-fluorenyl)dimethylmethane, and
(fluorenyl)(cyclopentadienyl)methyl)(1-(4-vinyl)phenyl)methane.

11. A process for producing a polymeric ligand in accordance with claim 1 wherein 1-(9-(2-vinyl)fluorenyl)-2-(9-fluorenyl) ethane is reacted with n-butyllithium to produce the polymeric ligand.

12. A process according to claim 5 wherein the polymeric ligand is prepared by reacting 1-(9-(2-vinyl)fluorenyl)-2-(9-fluorenyl), styrene, and azo bis isobutyronitrile.

* * * * *